(12) United States Patent
Van den Heuvel

(10) Patent No.: US 8,644,536 B2
(45) Date of Patent: *Feb. 4, 2014

(54) USER CONTROL FOR HEARING PROSTHESES

(75) Inventor: Koen Van den Heuvel, Hove (BE)

(73) Assignee: Cochlear Limited, Macquarie University, NSW (AU)

( * ) Notice: Subject to any disclaimer, the term of this patent is extended or adjusted under 35 U.S.C. 154(b) by 76 days.

This patent is subject to a terminal disclaimer.

(21) Appl. No.: 13/157,141

(22) Filed: Jun. 9, 2011

(65) Prior Publication Data

US 2011/0235814 A1 Sep. 29, 2011

Related U.S. Application Data

(62) Division of application No. 11/366,978, filed on Mar. 3, 2006, now Pat. No. 7,961,898.

(30) Foreign Application Priority Data

Mar. 3, 2005 (AU) ................................ 2005901007

(51) Int. Cl.
*H04R 25/00* (2006.01)

(52) U.S. Cl.
USPC ............................................. 381/314; 381/60

(58) Field of Classification Search
USPC ............ 381/58, 60, 312, 314, 315, 323, 326; 607/55, 56, 57; 600/559
See application file for complete search history.

(56) References Cited

U.S. PATENT DOCUMENTS

| 6,157,861 | A | 12/2000 | Faltys et al. |
| 7,561,920 | B2 | 7/2009 | Faltys et al. |
| 7,961,898 | B2 * | 6/2011 | Van den Heuvel ............ 381/314 |
| 2006/0178711 | A1 * | 8/2006 | Patrick et al. ................... 607/57 |

FOREIGN PATENT DOCUMENTS

| WO | WO-0205590 | 1/2002 |
| WO | WO-2004004412 | 1/2004 |

OTHER PUBLICATIONS

"Examiner's First Report on Australian Patent Application No. 2006200934", issued Nov. 18, 2010, 3 pages.

* cited by examiner

*Primary Examiner* — Huyen D Le
(74) *Attorney, Agent, or Firm* — Kilpatrick, Townsend & Stockton, LLP.

(57) ABSTRACT

A method of operating a hearing prosthesis. The hearing prosthesis includes memory and a clock and is configured to deliver stimuli to a user. The method includes determining the stimuli, with the hearing prosthesis, in response to a sound signal and at least in part by using one or more adjustable parameters stored in the memory. The method further includes receiving, from the user, a request to adjust at least one of the parameters, and determining whether to make the requested adjustment by reference to an amount of time, as determined by said clock, or a function based around an amount of time since a predefined event.

20 Claims, 4 Drawing Sheets

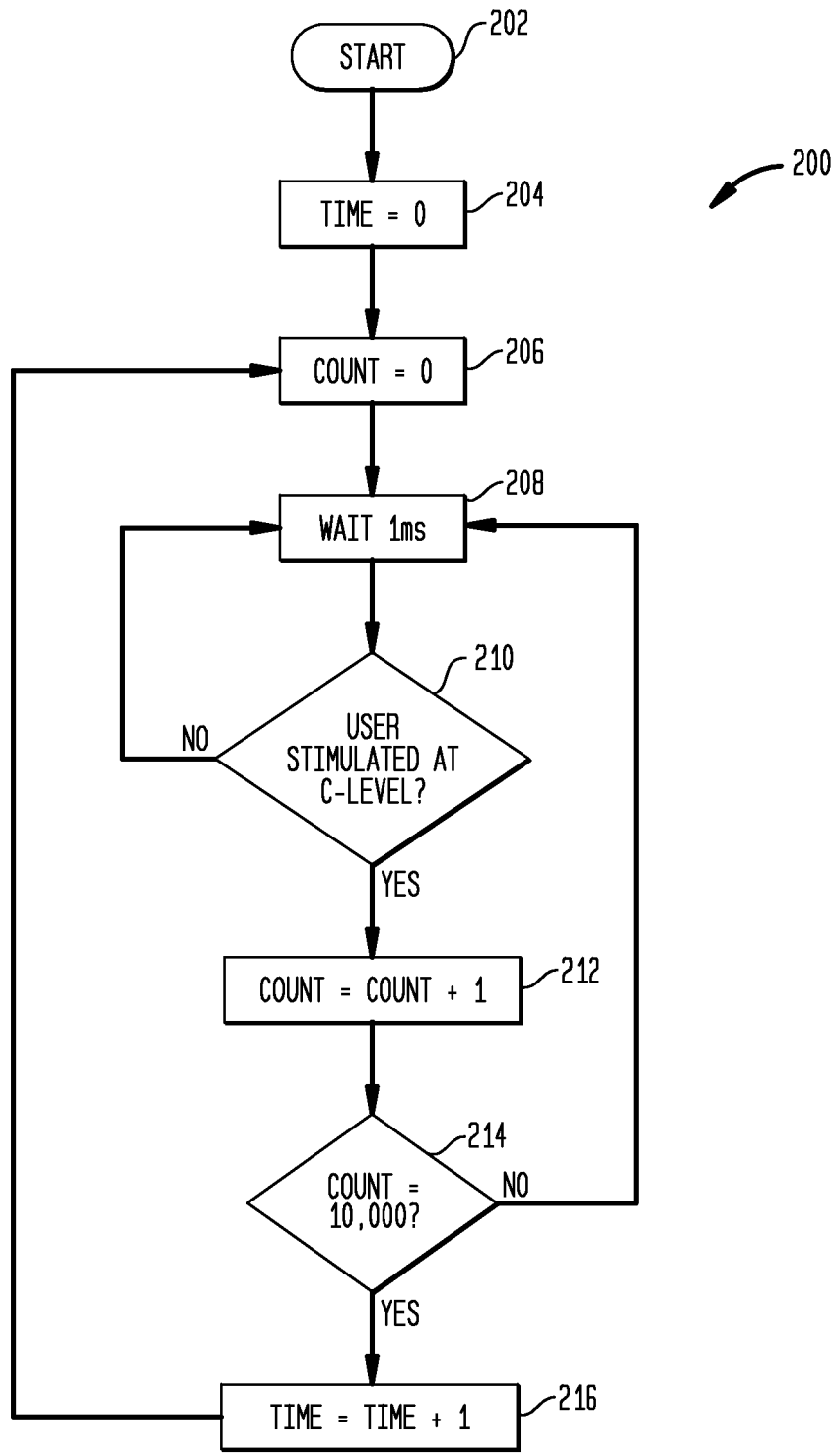

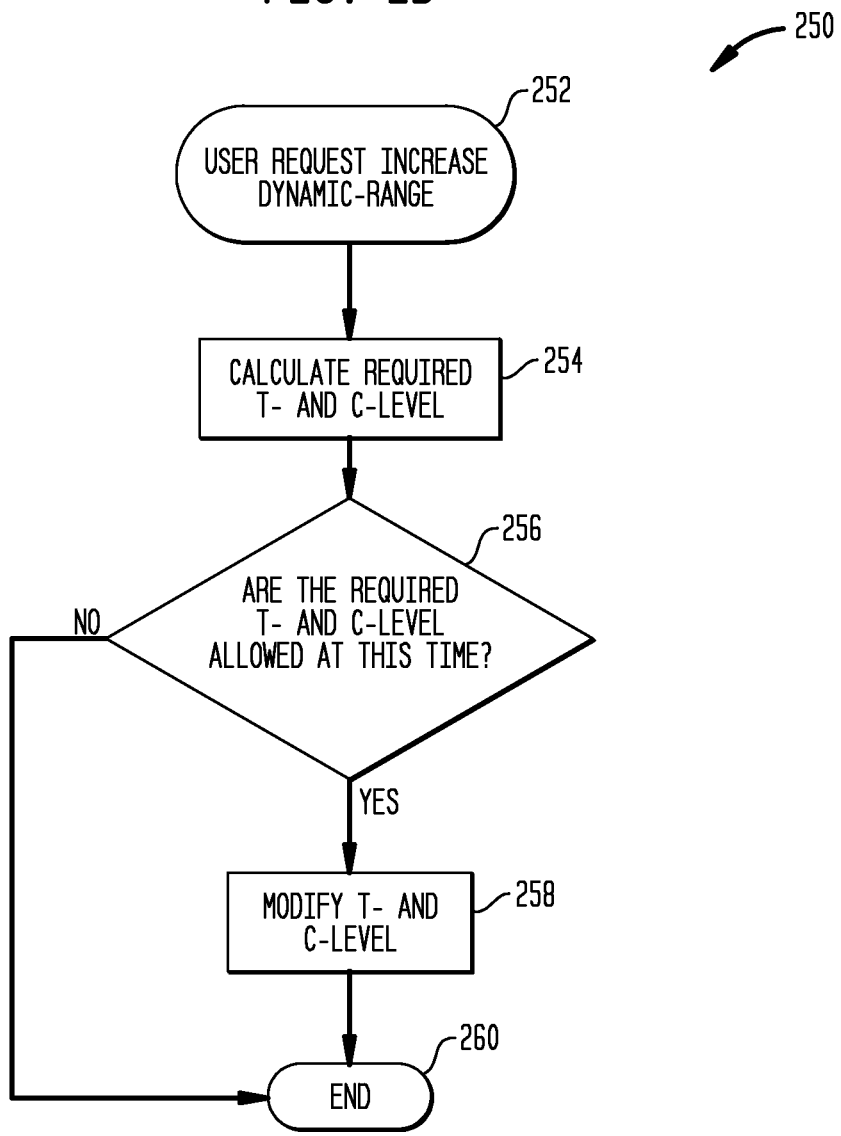

USER CONTROL FOR HEARING PROSTHESES

CROSS-REFERENCE TO RELATED APPLICATIONS

This application is a divisional application of U.S. patent application Ser. No. 11/366,978, filed on Mar. 3, 2006, and claims priority to Australian Patent Application No. 2005901007, filed on Mar. 3, 2005, and entitled, "User Control for Hearing Prostheses." The entire disclosure and contents of each of these documents is hereby incorporated by reference herein.

BACKGROUND

1. Field of the Invention

The present invention relates to hearing prostheses and, more particularly, to user control of a hearing prosthesis.

2. Related Art

Hearing prostheses, such as cochlear implants (also referred to as cochlear prostheses, cochlear devices, and the like; for simplicity hereinafter referred to as "cochlear implant") and hearing aids, are widely used to assist people with total or partial hearing loss. In general, modern devices of all types require the adjustment of operating parameters by skilled persons at the time of fitting.

For example, in the case of cochlear implants, after implantation there is a lengthy fitting process. The audiologist or clinician is required to create an initial map of electrodes, with various operating parameters for each electrode. The map is used to create the specific stimuli which are applied to the electrode, in accordance with the speech processing strategy employed by the particular implant system.

One of the more important operating parameters for each electrode is the dynamic range. This is generally set between two levels: the threshold or T level, which is the minimum stimulus which evokes a percept of sound, and the maximum comfortable or C level, which is the maximum stimulus which is not painful or damaging for the user (also referred to as the patient or recipient). It is desirable, for optimum perception of sound and speech by the user, that the dynamic range be correctly set. If it is too small, the range of amplitudes which can be perceived by the user is less than it could be, leading to a reduction in the range of different percepts which are possible and hence to reduced performance in speech perception. If the T level is too low, then stimuli are applied which cannot be perceived. If the C level is too high, then the patient may be overstimulated, leading to pain and possible injury to the patient.

It is known in some systems, for example in the Nucleus 4 system, to use a neural response based telemetry system to set a basic profile for each electrode. This is typically optimized by the clinician.

However, it is known that over time, and especially over the first few months of use, the dynamic range should be increased as the user becomes accustomed to the implant. Further, users may wish to have some control over the dynamic range of their implant.

Several approaches have been applied to address the issue of altering the dynamic range. For example, one approach is to use progressive maps, with increasing dynamic range, that are programmed into the speech processor. The patient may be encouraged, for example, to move to the next map each month. This needs to be done with great care, as the user may inadvertently choose the wrong map, and be overstimulated.

Another approach is to use the volume control of the map to allow the user to change the dynamic range. This approach also carries a risk that the user will select too large a dynamic range, and consequently be over-stimulated.

Another approach suggested has been to allow users to change their own profiles of T and C levels using shift and tilt controls. Again, this carries a risk that the user will select too large a dynamic range, and consequently be over-stimulated.

In the case of children, one of their parent(s) or caretaker(s) is/are generally the person/persons making such adjustments for the user. In many cases, they are cautious about altering settings, as they are concerned that the levels may become too loud for the child recipient. Consequently, they are often reluctant to use the existing systems to vary dynamic range. (In this and subsequent discussions, the term "user," "recipient," and "patient" is intended to encompass parent or caretaker in the case of children or other users having reduced capacity.

Although the foregoing is discussed mainly in the context of dynamic range, similar issues arise for other user adjustments. In some cases the incorrect adjustments may not potentially compromise safety, but they may produce suboptimal treatment for the patient.

SUMMARY

In one aspect of the present invention, a method of operating a hearing prosthesis is provided. The hearing prosthesis comprises memory and a clock and is configured to deliver stimuli to a user. The method comprises determining the stimuli, with said hearing prosthesis, in response to a sound signal and at least in part by using one or more adjustable parameters stored in the memory. The method further comprises receiving, from the user, a request to adjust at least one of the parameters, and determining whether to make the requested adjustment by reference to an amount of time, as determined by said clock, or a function based around an amount of time since a predefined event.

In another aspect of the present invention, a method of operating a hearing prosthesis is provided. The hearing prosthesis comprises memory and a clock and is configured to deliver stimuli to a user. The method comprises determining the stimuli, with said hearing prosthesis, in response to a sound signal and at least in part by using one or more adjustable parameters stored in the memory, and triggering, by reference to an amount of time, as determined by said clock, or a function based around an amount of time since a predefined event, the execution of a process to adjust one or more of the parameters.

In yet another aspect of the present invention, a method of operating a hearing prosthesis is provided. The hearing prosthesis comprises memory and a clock and is configured to deliver stimuli to a user. The method comprises determining the stimuli, with said hearing prosthesis, in response to a sound signal and at least in part by using one or more adjustable parameters stored in the memory. The method further comprises limiting the adjustment by the user of at least one of the parameters to a discrete maximum adjustment for a period determined by reference to an amount of time, as determined by said clock, or a function based around an amount of time since a predefined event.

BRIEF DESCRIPTION OF DRAWINGS

Implementations of the present invention will be described with reference to the accompanying figures, in which:

FIG. 2A is a flowchart showing the clock based control function of a software implementation of one embodiment of the present invention;

FIG. 2B is a flowchart showing control of user requests to increase dynamic range in accordance with one embodiment of the present invention.

DETAILED DESCRIPTION

Introduction to Selected Embodiments

Figure 1:
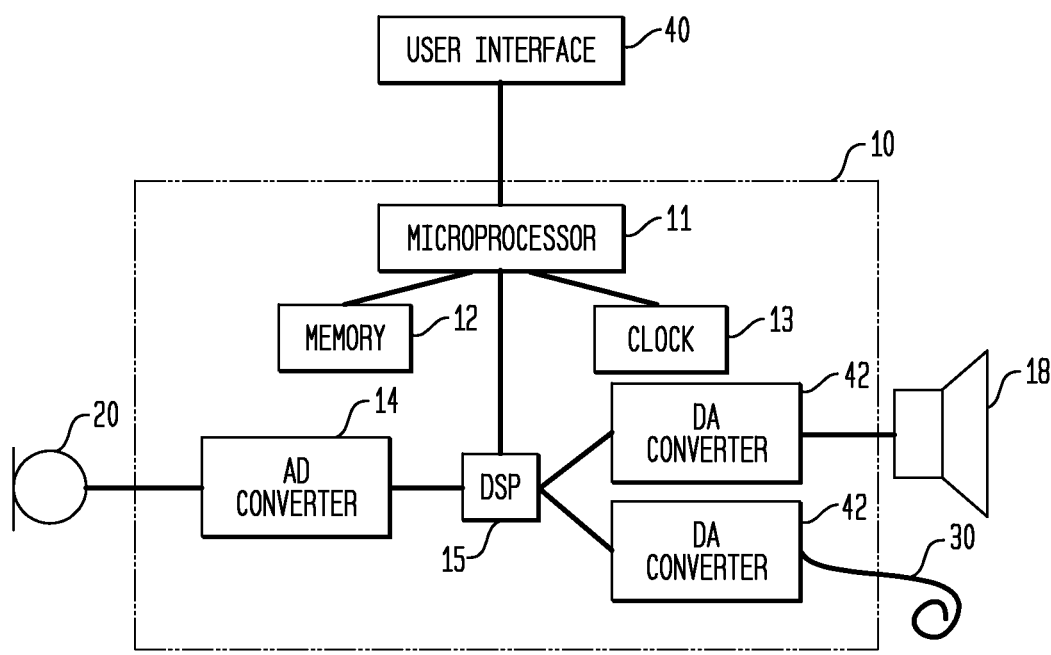
FIG. 1 is a functional schematic diagram of cochlear implant system in which embodiments of the present invention may be advantageously implemented.

The present invention is generally directed to providing a hearing prosthesis whereby the change of an operating parameter by the user is only possible in discrete maximum steps, with the availability for further increments being dependant upon some conditional event or occurrence ("condition" herein) represented by one or more condition parameters such as the time which has elapsed since some previous event. In embodiments in which the condition parameter(s) include an event, such event may be, for example, the initial fitting or adjustment by a clinician, the last user adjustment, the last upward adjustment by the user, etc. In certain embodiments, the condition parameter(s) may include, for example, an elapsed period of time, a certain quantity of stimuli at a particular current level, or some combination of time, stimulation count and stimulation level. In alternative embodiments, there may be a tiered set of increasing increments, of which more gradually are available over time.

According to one aspect, the present invention provides a hearing prosthesis including a processor and memory means, the prosthesis being adapted to deliver stimuli to a user, said stimuli being determined by software in response to a sound signal and at least in part by operating parameters stored in said memory means, wherein said prosthesis further includes a clock, and at least one of said operating parameters can be adjusted by the user, the adjustment being limited by reference to the time or a function of the time as determined by said clock since a predefined event. The prosthesis may be a hearing aid, cochlear implant or other device.

According to another aspect, the present invention provides a method for controlling the adjustment of operating parameters in a hearing prosthesis, the prosthesis including a processor and memory means and being adapted to deliver stimuli to a user, said stimuli being determined by software in response to a sound signal and at least in part by parameters stored in said memory means, said method comprising: providing a clock; said user selecting a condition parameter to adjust; permitting adjustment of said parameter, the extent of adjustment being limited by reference to the time or a function of the time as determined by said clock since a predefined event.

According to another aspect, the present invention provides a hearing prosthesis including a processor and memory means, the prosthesis being adapted to deliver stimuli to a user, said stimuli being determined by software in response to a sound signal and at least in part by operational parameters stored in said memory means, wherein said prosthesis further includes a clock, and wherein a process in said prosthesis is triggered by reference to the time or a function of the time as determined by said clock since a predefined event.

According to another aspect, the present invention provides a sound processor adapted to form part of a cochlear implant system, said processor including a processor and memory means, said sound processor being adapted to process sound signals and produce stimulation instructions for an implanted electrode array, said stimulation instructions being determined by software in response to a sound signal and at least in part by parameters stored in said memory means, wherein said sound processor further includes a clock, and at least one of said operating parameters can be adjusted by the user, the adjustment being limited by reference to condition parameters such as the time or a function of the time as determined by said clock since a predefined event.

According to another aspect, the present invention provides a computer program embodied on a computer readable medium for controlling the adjustment of operating parameters in a hearing prosthesis, the prosthesis including a processor and memory means, and being adapted to deliver stimuli to a user, said stimuli being determined by software in response to a sound signal and at least in part by parameters stored in said memory means, wherein said prosthesis further includes a clock, and at least one of said parameters can be adjusted by the user, the adjustment being limited by reference to the time or a function of the time as determined by said clock since a predefined event. Accordingly, the present invention allows for the use of an arrangement including a clock, so as to limit the extent of change permitting at a given time.

The term clock includes any means capable of measuring and/or indicating the passage of time, the number of instances one or more events have occurred, or some suitable combination of the two. Time may be, relevantly, the elapsed operating time of the prosthesis since some event. The function of the clock is to allow for measurement of a relevant elapsed time period, and/or count of events, and not merely the provision of regular timing pulses. Suitable clock devices may include, for example, a microprocessor clock having a crystal that vibrates at a regular frequency when an electrical current is applied to it, coupled with suitable software and memory, or a logical counter capable of recording instances a stimuli is at a pre-determined level.

The degree of operating parameter control required will vary with different users and for different parameters. Adjustment may be permitted of only one or a few operating parameters, or of a broader range of operating parameters, for an experienced user. The varying extent of user control permitted may be usefully controlled by the clinician during consultations.

The operating parameters which are suitable for adjustment will vary with the type of prosthesis and the way the particular device is configured. For example, for a cochlear implant, the operating parameters could include dynamic range (either for all, some, or selected groups of electrodes), T and C levels separately (again, either for all, some, or selected groups of electrodes), stimulation rate, pulse width or any other desired parameter. The adjustment could operate on a per-channel or group of channels basis, but where appropriate (e.g., dynamic range) it could permit changes across all channels.

Description of Exemplary Embodiments

The present invention will be further described with reference to a particular implementation suitable for a specific cochlear implant system. It will be understood that the present invention may be applied to other hearing prostheses now or later developed such as hearing aids or brain stem implants, or to other cochlear implant systems with modifications as required in those environments.

Further, the following discussion concentrates on adjustment of C levels in an electrode map. If other operating parameters are to be varied, it will be understood to apply the teachings of the present invention to such other operating parameters, and that the particular risks and therapeutic requirements for such operating parameters will need to be taken into account in setting the appropriate constraints and permissions.

Referring now to FIG. 1, an illustrative example of an implementation of the present invention is shown. Speech processor 10 includes a microprocessor 11 in communication with memory 12, clock 13, and DSP 15. Input sound signals from microphone 20 are received by AD converter 14 and passed to DSP 15. Under the control of microprocessor 11, DSP 15 processes the digitized sound signals, and outputs stimuli for use by the electrode array 30 and/or speaker 18.

It will be understood that there is considerable complexity in the speech processing software and in the selection of appropriate stimuli for delivery. The present invention is concerned with these aspects in as far as it concerns the adjustment of particular operating parameters, and accordingly, these aspects will not be described in further detail herein. Such systems are commercially available and understood by those of ordinary skill in the art. Similarly, the physical arrangements of the system will not be dealt with in detail. Parts of the present implementation may be physically placed in the implanted device, in the speech processor or even in a separate device which provides the user interface (for example in the form of a small remote control). The present invention may also be implemented in a totally implanted system for example as described in WO 2002/05590 in the in the name of Cochlear Limited. These are matters of implementation detail which depend upon the respective system.

In the system shown in FIG. 1, memory 12 stores an electrode map for the user. This map includes details and operating parameters for each electrode, including T and C values. Stimuli to be delivered via the respective electrode are selected so that their amplitude falls within the dynamic range defined by the T and C values. An example of a mapping procedure is described in WO2004/004412 in the name of Cochlear Limited.

User interface 40 is shown as a separate element, and may conveniently be in the form of a small remote control device as is conventionally used for control of digital hearing aids. Any alternative interface, such as controls on the speech processor or even user software on a personal computer (PC) or similar device may be used.

If the user determines that he would prefer to increase the C level, he inputs this request via the user interface 40. For the purposes of this example, we will assume that this is intended to increase the C level proportionately across all channels, although it will be appreciated that more specific requests per channel, channel groups, etc. could be treated similarly.

For example, the software may allow for a certain constrained increase once the user has been stimulated at the current maximum C level for 10,000 times across all channels since the last clinician visit. It may allow no increase until that level is increased. Alternatively, it may allow a proportionate increase based on the number of stimulations at that level. The increases may be permitted to set levels, preferably as an increment of the previous level, after certain numbers of stimulations at the current C level.

A more complex conditional function could also be used, based around time but taking into account numbers of stimulations as well. Alternatively, a purely time elapsed system could be used.

In one embodiment, the increase permitted is proportion of the current C levels, so that any increase must be moderate. Absolute limits could also be provided for the C level increases, even over time.

Account could also be taken of the time since the last increase.

FIG. 2A illustrates one way a clock-based control function could operate in the context of the present example. It will be understood that the particular operating parameter selected, C level, is arbitrary and the same or similar operations may be implemented to adjust any suitable operating parameter.

In the process 200 illustrated in FIG. 2A, after start block 202, a time value condition parameter is set at block 204 to a value of zero (t=0), and a time value condition parameter is set at block 206 to a value of zero (count=0). In subsequent operations, process 200 waits for a period (here, 1 ms) at block 208, then determines at block 210 if the user has been stimulated at the C level. If so, then the count value is incremented by one at block 212. If not, then after another wait at block 208, the operation at block 210 is repeated. The incrementing of the count value at block 212 maintains the count of how often the user has been stimulated at the C level. The process then tests if the count exceeds, in this example, the 10,000 count level. If so, the time is incremented, and the above process is repeated as shown in FIG. 2A. If the count is not at 10,000, then counting process continues to repeat.

FIG. 2B is a flowchart of a process 250 illustrating one embodiment of the operations which may be performed in response to a user's request to adjust the dynamic range of the hearing prosthesis. At block 250 a user requests an increase of the dynamic range (it should be appreciated that the dynamic range is also considered to be an operating parameter, albeit one defined by two other operating parameters, V, T and C levels.). The required T and C levels are calculated at block 254. By referring to criteria, for example the count and time condition parameters of FIG. 2A, or the values of any other condition parameters representative of the selected condition, process 250 determines at block 256 if increase as requested is allowed, and modifies the levels at block 258 if permitted. Process 250 then ceases at block 260.

Figure 3:
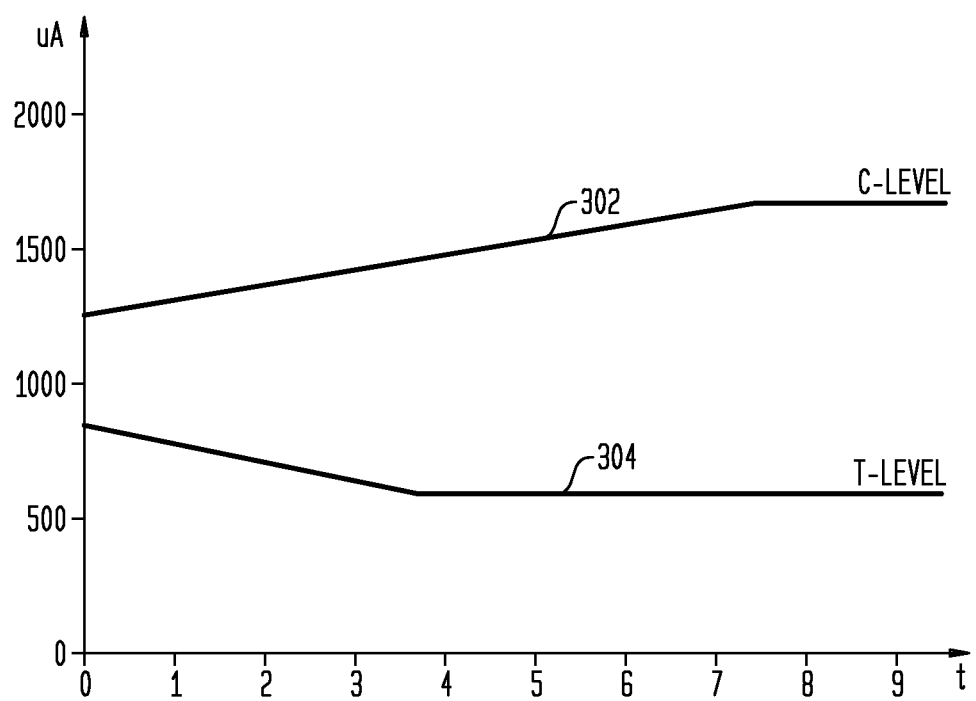
FIG. 3 is a graph showing constraints on C level adjustment which it may be desirable to impose on a user, in accordance with one embodiment of the present invention.

FIG. 3 illustrates graphically how user control limitations correspond to the expected permitted increase over time. The time axis is in units of months. It is expected that the C level 302 should increase, and the T level 304 decrease over time after implantation, so that the dynamic range increases. The parameters setting permission to increase the dynamic range may be dependent on a conservative estimate of expected changes to the C and T levels. As the number of stimulations at the C level over time increases, the permitted increase cumulatively rises.

It will be understood that this process may be applied to other parameters in a similar manner. The provision of a clock as a cumulative measure allows the use of sophisticated gradual control by the user. It is also noted that the clock function may be implemented in various ways, in combination with other components and functions, and should not be understood as limited to the particular implementation described.

The process may also be used in association with other measures. For example, the clock and stimulation count may be used to trigger either an automatic or user-driven automatic recalibration of C and T levels, using the systems already provided for this purpose in some commercially available systems. Alternatively, after certain time/stimulation counts the user could be prompted to subjectively set C and T levels based upon signals generated by a test mode of the speech processor. It will be appreciated that a wide variety of measures can be potentially controlled in this way, and the parameters should be understood to include matters extending beyond strictly the operating parameters of the cochlear implant, or other auditory prosthesis.

Although the present invention has been fully described in conjunction with several embodiments thereof with reference to the accompanying drawings, it is to be understood that various changes and modifications may be apparent to those skilled in the art. For example, in the above embodiments the operations performed to limit the adjustment increments of the operating parameters are performed in software executing on a processor or microprocessor. It should be understood, however, that in alternative embodiments of the present invention may be implemented in computer hardware such as in an ASIC, or other hardware now or later developed. It should also be appreciated that the parameters that are considered by embodiments of the present invention, when determining the increment of the adjustment limits of the operating parameters; that is, the condition parameters may include operating parameters. In other words, for some parameters, it is the use of the parameter which will dictate whether or not it is considered to be a conditioned parameter, an operating parameter, or both. Such changes and modifications are to be understood as included within the scope of the present invention as defined by the appended claims, unless they depart therefrom.

What is claimed is:

1. A method of operating a hearing prosthesis comprising memory and a clock, the hearing prosthesis configured to deliver stimuli to a user, the method comprising:
    determining the stimuli, with said hearing prosthesis, in response to a sound signal and at least in part by using one or more adjustable parameters stored in the memory;
    receiving, from the user, a request to adjust at least one of the parameters; and
    determining whether to make the requested adjustment by reference to an amount of time, as determined by said clock, or a function based around an amount of time since a predefined event.

2. The method of claim 1, further comprising:
    preventing the requested adjustment of the at least one of the parameters in response to the determination of whether to make the requested adjustment.

3. The method of claim 1, further comprising:
    adjusting the at least one of the parameters in accordance with the requested adjustment in response to the determination of whether to make the requested adjustment.

4. The method of claim 1, wherein the function based around an amount of time comprises:
    one or more of the time elapsed since the event, the quantity of times at least one of the parameters has been utilized since the event, or a measure of the cumulative use of at least one of the parameters since the event.

5. The method of claim 1, wherein the event is at least one of a fitting of the prosthesis, a last adjustment of the prosthesis by a clinician, and a last adjustment of one of the parameters.

6. The method of claim 1, wherein the prosthesis is a cochlear implant comprising an implanted stimulator and a speech processor, and said determining whether to make the requested adjustment is performed by the speech processor.

7. The method of claim 1, wherein the request to adjust at least one of the parameters is a request to adjust at least one parameter for fewer than all channels of the hearing prosthesis.

8. A method of operating a hearing prosthesis comprising memory and a clock, the hearing prosthesis configured to deliver stimuli to a user, the method comprising:
    determining the stimuli, with said hearing prosthesis, in response to a sound signal and at least in part by using one or more adjustable parameters stored in the memory; and
    triggering, by reference to an amount of time, as determined by said clock, or a function based around an amount of time since a predefined event, the execution of a process to adjust one or more of the parameters.

9. The method of claim 8, wherein the process to adjust one or more of the parameters comprises:
    prompting the user to recalibrate the one or more of the parameters.

10. The method of claim 8, wherein the process to adjust one or more of the parameters comprises:
    recalibrating the one or more of the parameters automatically.

11. The method of claim 8, wherein the event is at least one of a fitting of the prosthesis, a last adjustment of the prosthesis by a clinician, and a last adjustment of one of the parameters.

12. The method of claim 8, wherein the function based around an amount of time comprises:
    one or more of the time elapsed since the event, the quantity of times at least one of the parameters has been utilized since the event, or a measure of the cumulative use of at least one of the parameters since the event.

13. The method of claim 8, wherein the process to adjust one or more of the parameters comprises:
    adjusting at least one of a C-level and a T-level of the hearing prosthesis.

14. The method of claim 8, wherein the process to adjust one or more of the parameters comprises:
    adjusting at least one of a stimulation rate and a pulse width of the hearing prosthesis.

15. A method of operating a hearing prosthesis comprising memory and a clock, the hearing prosthesis configured to deliver stimuli to a user, the method comprising:
    determining the stimuli, with said hearing prosthesis, in response to a sound signal and at least in part by using one or more adjustable parameters stored in the memory;
    limiting the adjustment by the user of at least one of the parameters to a discrete maximum adjustment for a period determined by reference to an amount of time, as determined by said clock, or a function based around an amount of time since a predefined event.

16. The method of claim 15, wherein the function based around an amount of time comprises:
    one or more of the time elapsed since the event, the quantity of times at least one of the parameters has been utilized since the event, or a measure of the cumulative use of at least one of the parameters since the event.

17. The method of claim 15, wherein the event is at least one of a fitting of the prosthesis, a last adjustment of the prosthesis by a clinician, and a last adjustment of one of the parameters.

18. The method of claim 15, further comprising:
    changing the size of the discrete maximum adjustment based on a current value of the at least one parameter.

19. The method of claim 15, further comprising:
varying the discrete maximum adjustment based on a time period commencing upon the occurrence of the predefined event or another event.

20. The method of claim 15, further comprising:
varying the discrete maximum adjustment over time to provide a tiered set of increasing discrete maximum adjustment values for the at least one parameter.

* * * * *